(12) United States Patent  (10) Patent No.: US 6,710,357 B1
Schweitzer  (45) Date of Patent: Mar. 23, 2004

(54) TOP AND BOTTOM ULTRAVIOLET STERILIZATION SYSTEM

(75) Inventor: Todd Schweitzer, Torrance, CA (US)

(73) Assignee: UV Doctor LLC, Las Vegas, NV (US)

( * ) Notice: Subject to any disclaimer, the term of this patent is extended or adjusted under 35 U.S.C. 154(b) by 0 days.

(21) Appl. No.: 10/172,519

(22) Filed: Jun. 14, 2002

(51) Int. Cl.$^7$ ................................................. A61L 2/00
(52) U.S. Cl. ........................ 250/492.1; 422/22; 422/24; 422/28
(58) Field of Search ............................. 422/22, 24, 28; 250/492.1

(56) References Cited

U.S. PATENT DOCUMENTS 5,744,094 A * 4/1998 Castberg et al. .............. 422/24

* cited by examiner

Primary Examiner—John R. Lee
Assistant Examiner—Erin-Michael Gill
(74) Attorney, Agent, or Firm—Charles H. Thomas

(57) ABSTRACT

The present invention involves a system for irradiating articles with ultraviolet radiation that are transported through an irradiation tunnel along a longitudinal article treatment path from a tunnel entrance to a tunnel exit employing a conveyor system. Ultraviolet irradiation sources are located within the tunnel, both above and below the article treatment path. The conveyor system includes at least two different sequential segments that contact different laterally separated locations on the articles to be treated from beneath. The points of contact between the different segments of the conveyor system are offset in a lateral or transverse direction so that all locations on the articles are left unobscured from beneath at some location on the treatment path. As a consequence, all downwardly facing surfaces of the articles carried on the conveyor system are exposed to radiation from beneath. The ultraviolet irradiation sources may be configured as elongated, transverse tubes, at least some of which are located within elliptical reflectors so that some of the ultraviolet radiation is reflected onto the passing articles at angles that vary as the articles progress along the treatment path. The ends of the ultraviolet tubes are mounted within unique end supports that allow the tubes to be rotated one hundred eighty degrees by a single person manipulating just one end of each lamp tube.

15 Claims, 6 Drawing Sheets

TOP AND BOTTOM ULTRAVIOLET STERILIZATION SYSTEM

BACKGROUND OF THE INVENTION

1. Field of the Invention

The present intervention relates to an improved system for sterilizing articles utilizing ultraviolet radiation.

2. Description of the Prior Art

At present, food packaging products such as dairy product cartons, lids, sealing films, plastic wrap, labels, reusable product containers and other articles used in the packaging of products are sanitized by ultraviolet irradiation. In conventional food packaging and container sanitizing operations the articles to be treated are passed on a conveyor beneath a conventional lamp that emits ultraviolet radiation. The ultraviolet lamp is driven by a magnetic ballast. In order to irradiate and thereby thoroughly sanitize articles on the conveyor system the undersides of the articles resting upon the conveying mechanism must be irradiated, as well as the upper sides.

To irradiate the underside of an article, it has been conventional practice to employ a conveyor belt having an open mesh through which a source of ultraviolet illumination shines. Alternatively, the articles to be irradiated may be placed upon a plurality of narrow, laterally separated belts or chains that support the articles to be irradiated from beneath and convey them through the irradiation tunnel. However, even though both of these conventional systems allow significant portions of the underside of articles transported through the irradiation tunnel to be exposed to ultraviolet radiation, the structures of conventional conveyor systems of this type do cast radiation "shadows" on certain portions of the undersides of the articles being treated. As a consequence, these articles cannot be completely sanitizing by ultraviolet radiation using conventional conveyor systems.

A further difficulty in sanitizing articles conveyed past an ultraviolet irradiation source is that the presence of surfaces parallel to the rays of the irradiation source and also indentations and other nooks and crannies in the articles prevents the ultraviolet radiation from striking all of the surfaces of the articles. Consequently, bacteria can linger untreated in areas on the surfaces of the articles that do not receive direct or reflected ultraviolet radiation.

Still another problem that exists in conventional ultraviolet irradiation tunnels is that the lamps emitting the ultraviolet radiation tend to deteriorate rather rapidly, particularly if they are constructed as elongated tubes. Nevertheless, an elongated tubular shape for the ultraviolet irradiation sources is the best shape for irradiating the entire width of the irradiation tunnel.

The problem that arises is that conventional ultraviolet radiation lamp tubes are supported at their ends, but are unsupported between their ends. Any support between the ends of the tubes would interfere with the radiation emitted. As a consequence, with the intense heat that is built up in the generation of ultraviolet radiation, the tubular structure of the ultraviolet radiation lamps softens and tends to sag at the centers of the lamps. When this occurs radiation is irregular and at a reduced intensity. Also, this deformation of the bodies of the tubes causes structural damage, leading to premature failure of the ultraviolet radiation lamps. The longer the tubes, the greater the likelihood of damage in this connection. Some ultraviolet tubes can have a length as great as 10 feet.

To solve this problem it is conventional practice to periodically rotate the elongated ultraviolet radiation tubes one hundred eighty degrees to reduce the distortion to the structure of the lamp tubes caused by sagging at their centers. This maintenance procedure does prolong the life of the lamp, but requires the combined effort of two persons to rotate each lamp. That is, the supports at both ends of the ultraviolet radiation lamp tubes on both sides of the tunnel must be accessible. This is often difficult or inconvenient, since one side of the tunnel may be located close to a wall of a room in which the tunnel is located. In any event, the individuals performing the task must coordinate their efforts and simultaneously remove the ends of the lamp tubes from their supports and rotate the ends of the tubes one hundred eighty degrees. The ends of the tubes must then be replaced in their supports. This maintenance process is therefore rather time-consuming and requires two people.

SUMMARY OF THE INVENTION

The present invention provides an improved system for irradiating articles with ultraviolet radiation within an irradiating tunnel that largely solves the foregoing problems. The system of the present intervention greatly reduces or eliminates completely the problem of "shadows" being cast upon portions of the articles as they are conveyed through the tunnel. The system of the invention also provides a construction that allows a single person to rotate an ultraviolet radiation tube one hundred eighty degrees and reseat it in its support. The unique system of the invention greatly improves the degree of sanitation that is achieved using ultraviolet radiation upon articles conveyed past an ultraviolet irradiation source.

The invention involves a system for irradiating generally flat or collapsible objects such as reusable produce shipping boxes and food packaging materials that have various crevices, openings, and other niches in which bacteria can collect, or even just surfaces that are perpendicular to the path of travel of the articles through the tunnel. In conventional systems in which the objects are transported on a conveyor chain, there is always a "shadow" cast by the conveyor chain or drive on the undersides of the items being irradiated as the articles are transported through an irradiation tunnel. These shadows prevent the article from being completely irradiated.

According to the improvement of the invention, the drive chains or belt system upon which the objects are supported is divided into segments in which the conveyor chains or belts of each sequential segment are laterally offset from the conveyor chains of the adjacent conveyor segment or segments. Thus, although a conveyor chain or belt of one segment will cast a shadow on the location of the underside of the article to be irradiated, the shadows are cast upon a different part of the article in the next sequential segment. As a consequence, as the object passes through the tunnel, at one point or another the entire undersurface, as well as the upper surface, is irradiated so that there is no sheltered, shadowed region on the underside of the articles being conveyed. To the contrary, all areas of the undersurface of the article are exposed to ultraviolet radiation sometime during the progression of the article along its path of travel.

A further feature of the invention is the use of nonparabolic reflectors, such as elliptical reflectors. In conventional practice the elongated, tubular ultraviolet radiation lamps are located above and beneath a conveyor system. To maximize the ultraviolet radiation directed at the articles being transported by the conveyor system each elongated ultraviolet lamp is provided with a concave reflector located behind the lamp and facing the articles being transported through the irradiation tunnel. The axis of the lamp is located within the arc of curvature of the reflector. It has been accepted practice in conventional practice for the reflectors to be constructed with a parabolic cross section. As a consequence, ultraviolet radiation that is reflected from the conventional parabolic reflectors travels in parallel paths to impinge upon articles passing on a conveyor system therebeneath.

While such a construction does provide for reflection along the shortest path to reach the article, the fact that the reflected radiation travels in parallel rays means that the reflected radiation is always directed at the article perpendicular to its path of travel. Consequently, surfaces of the article that are oriented perpendicular to the path of travel receive little, if any radiation. The same is true of indentations, niches, slots, and undercuts on the article. These regions are sheltered from the impinging radiation by other portions of the article. With conventional parabolic reflectors, the irradiating light is focused in parallel beams onto the articles passing therebeneath or thereabove. This causes certain surfaces on the article normal to the path of travel, as well as crevices and indentations in the articles to pass through the system without receiving direct ultraviolet radiation.

The improved ultraviolet radiation conveyor system of the present invention greatly alleviates this problem by constructing the reflectors with nonparabolic surfaces which may be elliptical, rather than of a parabolic cross section. With an elliptical reflector the irradiating illumination strikes the surfaces of the articles at different angles as the articles move past the irradiating lamps. Consequently, at some point in the progression of each article along its path of travel the various nooks and indentations in the article receive reflected illumination at an angle from one or more of the irradiating lamps.

A further feature of the invention is the mounting system for the ultraviolet lamps. The ultraviolet lamps are shaped generally as elongated tubular structures, and look much like conventional fluorescent light bulbs in conventional overhead room lighting systems. With the intense heat generated by the emission of ultraviolet radiation, the tubular ultraviolet lamps tend to soften and at their centers. Also, the sides of the lamps facing the reflectors are subject to a much higher level of heat than the sides of the lamps facing the articles passing therebeneath. Therefore, it is advantageous to periodically rotate the lamps about their axes to extend their useful life. In conventional systems this requires two workers, one at each end to lift both ends of the lamps in order to rotate them.

With the mounting system of the present system, one end of each lamp is inserted through an opening, preferably circular, that has a diameter slightly larger than the diameter of the lamp. The other end of the lamp is held by an oblong or bar-shaped constraint. To rotate the lamp, the rectangular bar-shaped constraint is merely lifted out of its inverted U-shaped yoke or saddle, rotated about its own axis one hundred eighty degrees, and reinserted back into the inverted U-shaped saddle. The clearance provided by the opening in the support at the opposite end of the lamp allows the lamp to be tilted while that end rotates in its circular opening. Consequently, the lamp can be rotated by a single person standing at one end of the lamp.

In one broad aspect the present invention may be considered to be an ultraviolet light irradiation apparatus comprising an irradiation tunnel, a conveyor system, at least one upper ultraviolet irradiation source, and at least one lower ultraviolet irradiation source. The tunnel is of conventional construction having an entrance and having an exit longitudinally displaced from the entrance. The conveyor system supports articles to be irradiated from beneath and transports them along a longitudinal treatment path from the entrance to the exit of the tunnel.

Unlike conventional conveyor systems, the conveyor system of the invention includes a plurality of different longitudinally sequential segments. The different sequential segments of the conveyor system contact different laterally separated locations on the articles from beneath. In this way all locations on the article are left unobscured from the irradiation source from beneath at some location on the treatment path within the irradiation tunnel between the entrance and exit thereof. The upper ultraviolet irradiation source is located within the irradiation tunnel for irradiating the articles from above as they are transported along the treatment path. The lower ultraviolet irradiation source irradiates the articles from beneath at the plurality of different longitudinally sequential segments of the conveyor system.

Preferably, each of the different conveyor segments is comprised of a plurality of longitudinally extending, endless conveyor loops lying in parallel, longitudinally aligned, vertical planes spaced apart from each other in a direction perpendicular to the treatment path. The planes in which the endless conveyor loops are aligned on at least two of the different sequential conveyor segments are offset from each other in a direction perpendicular to the treatment path. The endless conveyor loops have longitudinally opposing end extremities. Preferably also, the end extremities of the conveyor loops of each of the conveyor segments overlap and are interleaved between the end extremities of the conveyor loops of each longitudinally adjacent conveyor segment.

To insure adequate irradiation coverage across the width and throughout the length of the irradiation tunnel, at least some of the ultraviolet irradiation sources are often constructed as elongated tubes aligned transverse to the longitudinal path of travel. A plurality of the transverse, upper ultraviolet radiation tubes are located within the tunnel at longitudinal intervals from each other. In the preferred arrangement at least one of the transverse, lower ultraviolet radiation tubes is located beneath the treatment path at each of the different longitudinally sequential conveyor segments.

In another broad aspect the invention may be considered to be a method of irradiating articles utilizing a conveyor system that transports the articles and supports them from beneath along a longitudinal treatment path from an entrance to an exit of an irradiation tunnel. At least one upper ultraviolet irradiation source is located above the longitudinal treatment path and at least one lower ultraviolet irradiation source is located beneath the longitudinal treatment path.

The method of the invention involves supporting the articles from beneath and changing the laterally separated points of contact thereon at different longitudinal locations along the tunnel as the articles are transported along the longitudinal treatment path. This process prevents any parts of the articles facing the irradiation sources from being shadowed from radiation throughout the entire length of the longitudinal treatment path. Preferably, the articles are subjected to ultraviolet radiation from beneath at a plurality of different longitudinal locations along the tunnel. The method of the invention preferably further involves reflecting at least some of the ultraviolet light from at least one of the ultraviolet irradiation sources to thereby irradiate the articles with reflected ultraviolet light that impinges upon the articles at angles that vary as the articles are transported past the ultraviolet irradiation source or sources.

In still another aspect the invention may be considered to be an improvement in an ultraviolet irradiation tunnel in which articles to be irradiated are transported along a longitudinal path past an elongated, ultraviolet irradiation source. The improvement of the invention comprises a concave reflector having a nonparabolic cross-sectional arc of curvature. The reflector faces the longitudinal path. The elongated ultraviolet irradiation source is located within the arc of curvature and between the reflector and the longitudinal path. Since the arc of curvature of the reflector is nonparabolic, light emitted from the irradiation source and reflected by the reflector strikes the passing articles to be sanitized by ultraviolet radiation at different angles as the articles move past the reflector. Preferably the arc of curvature of the reflector has an elliptical shape and a plurality of irradiation sources and reflectors are located at longitudinally separated locations both above and below the longitudinal path. As a consequence, reflected radiation reaches crevices, niches, and surfaces perpendicular to the path of travel to a much greater extent than in conventional irradiation tunnels.

In still another aspect, the invention may be considered to be an improvement in an ultraviolet irradiation tunnel in which articles to be irradiated are transported along a longitudinal path past an elongated, horizontally oriented, ultraviolet radiation lamp having opposing ends. A pair of opposing ultraviolet lamp supports are provided for mounting the opposing ends of the elongated lamp relative to the tunnel. According to the improvement of the invention a first of the ultraviolet lamp supports is secured relative to the ultraviolet irradiation tunnel and has an opening therethrough, preferably circular, to receive one of the ultraviolet lamp ends. The second support includes a noncircular constraint that is secured to the other of the opposing ultraviolet lamp ends. A saddle or yoke is secured relative to the tunnel at approximately the same height as the first ultraviolet lamp support. This saddle receives the noncircular constraint in either of two oppositely oriented dispositions. This allows the ultraviolet lamp to be oriented horizontally alternatively to face in either of two opposite directions.

Preferably the noncircular constraint is an oblong block which may have a rectangular configuration. The saddle then defines an upwardly facing channel having vertical sides and a horizontal bottom and is configured to receive and snugly seat the rectangular constraint therewithin. The opening through the first of the ultraviolet lamp supports is large enough to permit the elongated lamp to be tilted relative to the first of the ultraviolet lamp supports.

The invention may be described with greater clarity and particularity by reference to the accompanying drawings.

DESCRIPTION OF THE EMBODIMENT

Figure 1:
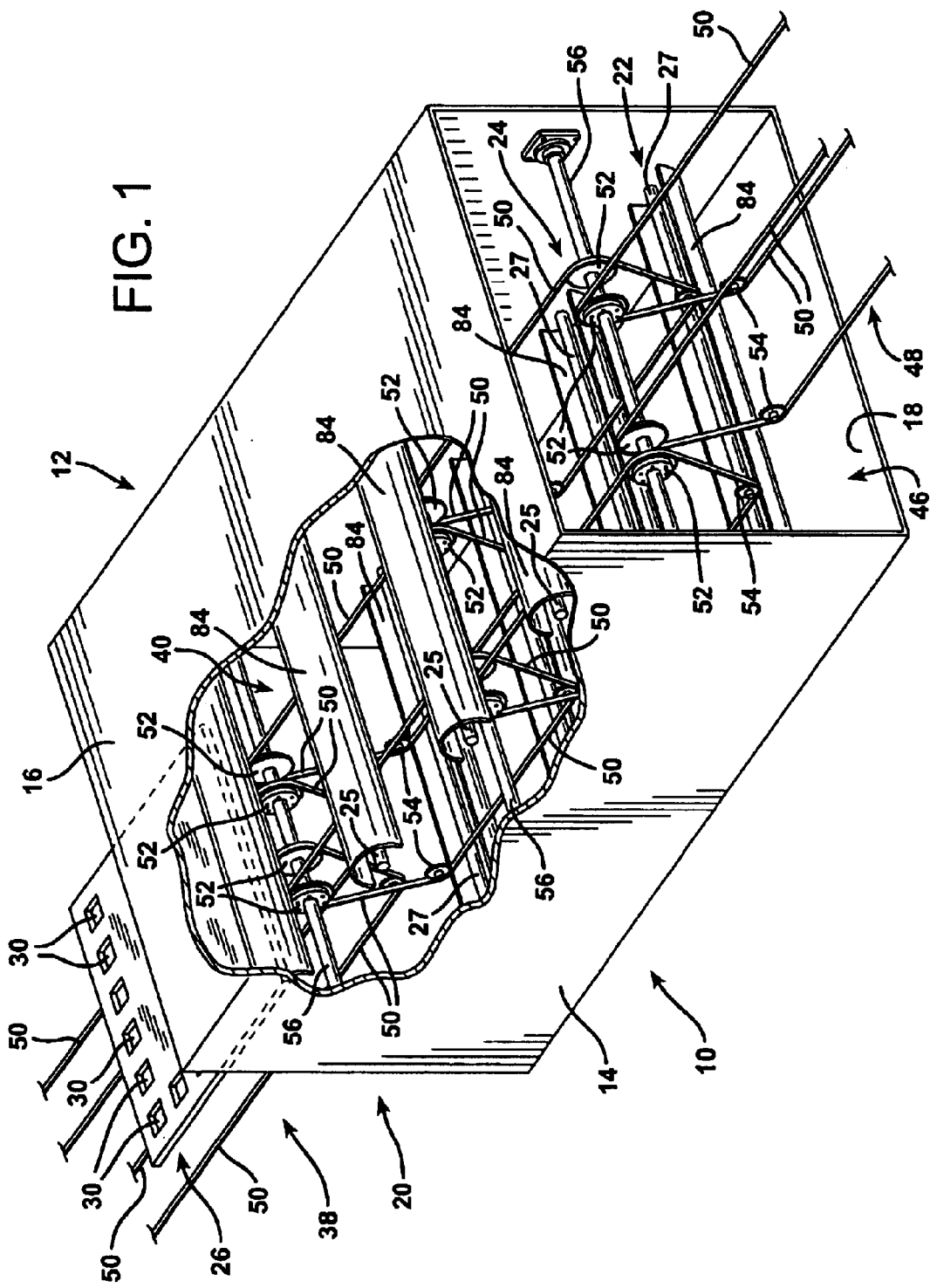
FIG. 1 is a perspective view, partially broken away, of an improved ultraviolet irradiation tunnel and conveyor system constructed according to the present invention.
Figure 3:
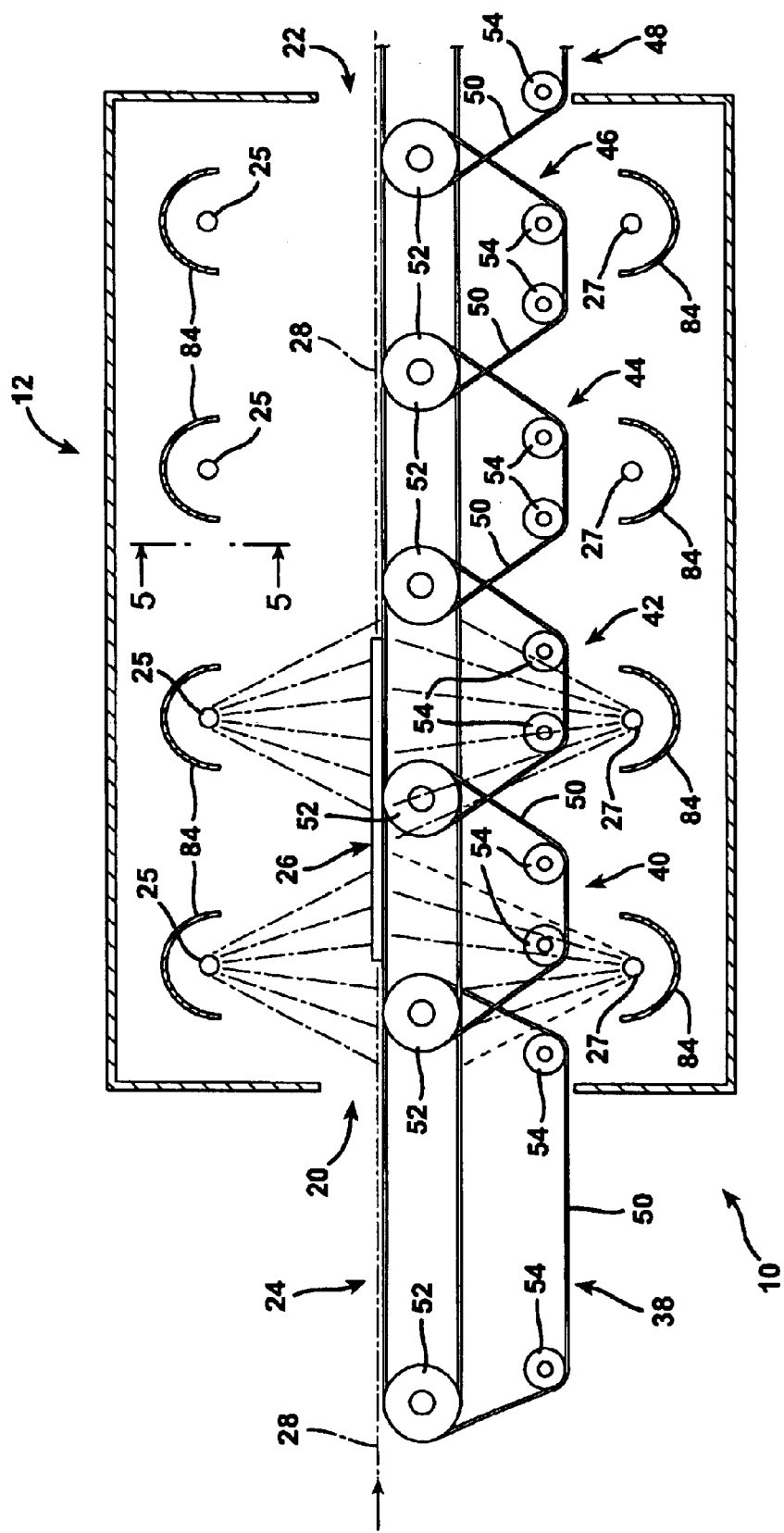
FIG. 3 is a side, sectional elevational view of the tunnel and conveyor system illustrated in FIG. 1.

FIGS. 1 and 3 illustrate an improved ultraviolet light irradiation apparatus according to the invention indicated generally at 10. The irradiation apparatus 10 is comprised of an irradiation tunnel 12 having laterally separated vertical sidewalls 14, a roof 16, and a floor 18. The ends of the tunnel 12 have openings that define an entrance 20 and an exit 22 which are longitudinally displaced from each other.

A conveyor system, indicated generally at 24, is provided for supporting articles 26 to be irradiated with ultraviolet radiation. The articles 26 to be irradiated are supported from beneath by the conveyor system 24 and are transported along a linear, horizontal, longitudinal treatment path 28 from the entrance 20 to the exit 22 of the tunnel 12. As the articles 26 pass along the treatment path 28, they are exposed to ultraviolet radiation from above by a bank of upper ultraviolet lamps 25 and to ultraviolet radiation from beneath by a bank of lower ultraviolet radiation lamps 27. The ultraviolet lamps 25 and 27 are preferably custom germicidal medium pressure lamps and preferably emit ultraviolet radiation having a wavelength of between about 250–260 nm. Ultraviolet light within this bandwidth is most effective for destroying microorganisms on the articles 26 to be treated. The lamps 25 and 27 are preferably water cooled and rated at 300 watts per inch (wpi).

The articles 26 may be virtually any shape, but for simplicity of illustration are shown as being formed as flat, slablike structures having a multiplicity of openings 30 defined therethrough. Consequently, the articles 26 are each depicted as having a flat, horizontal upper surface 32, a flat horizontal undersurface 34, and vertical surfaces 36 around the edges of the articles 26 and at the openings 30 therein.

Figure 2:
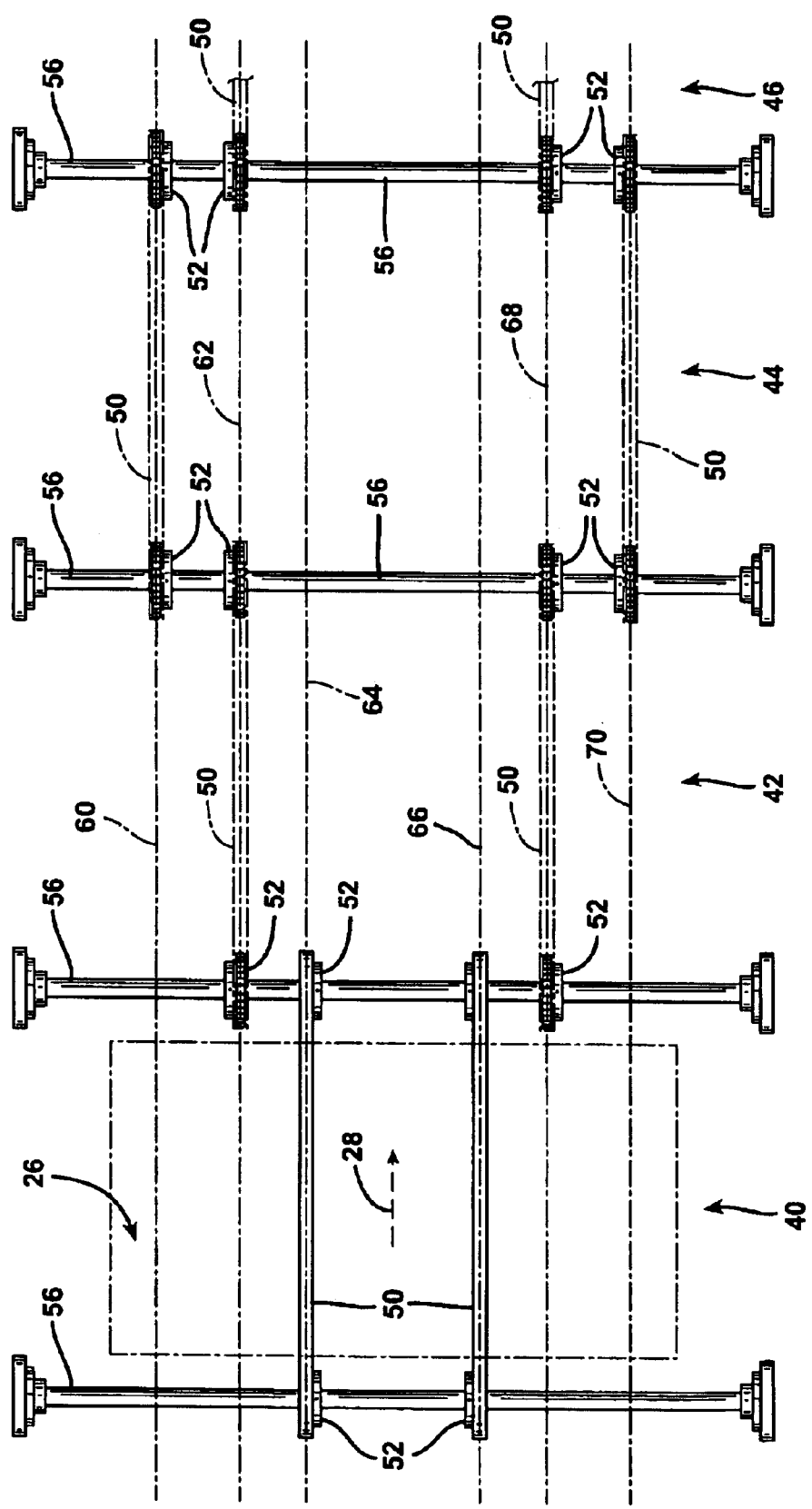
FIG. 2 is a diagrammatic top plan view of a portion the improved conveyor system shown in FIG. 1.
Figure 8:
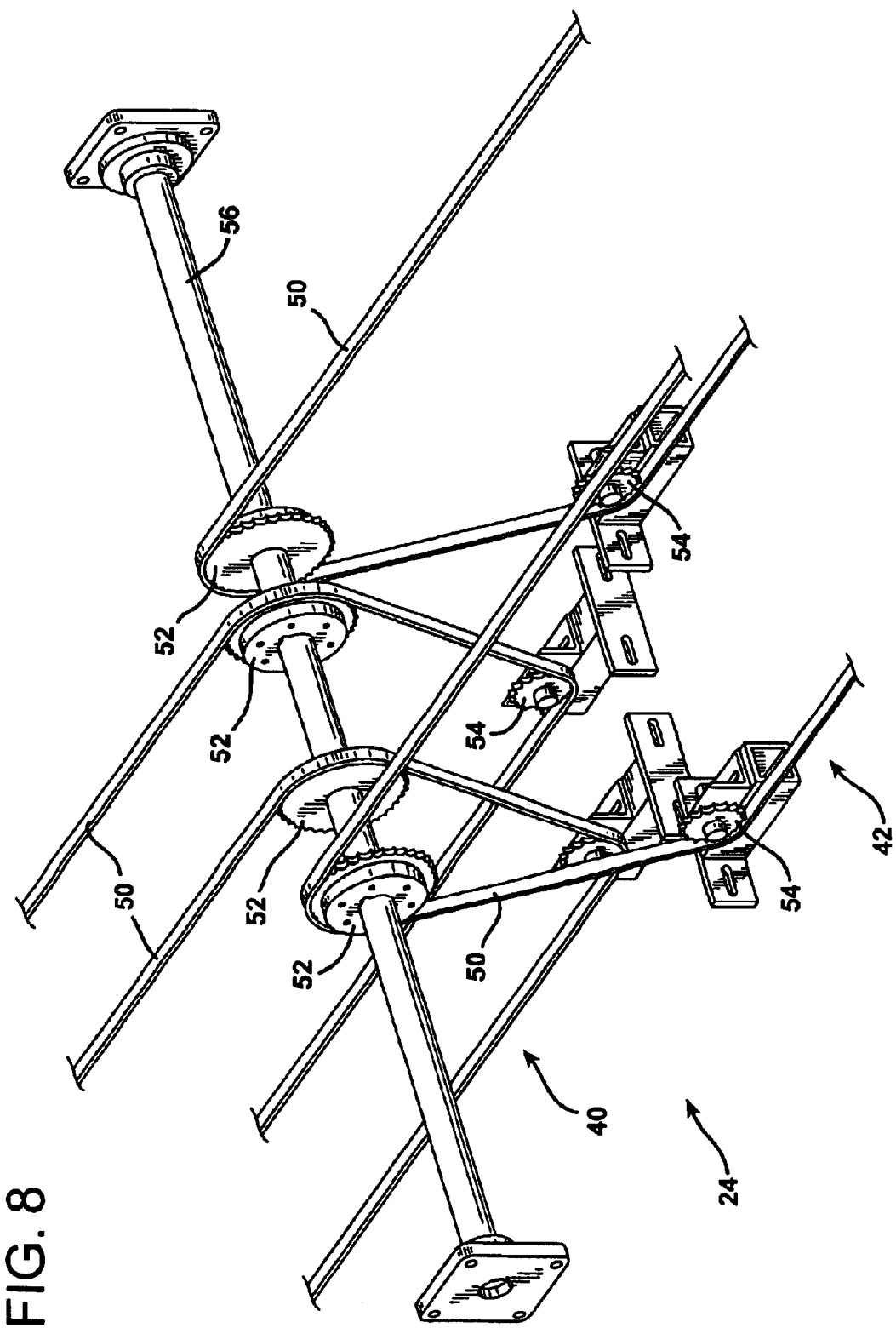
FIG. 8 is a perspective detail showing the interleaved ends of two of the conveyor segments employed in the irradiation tunnel of FIG. 1.

The conveyor system 24 is comprised of a plurality of different longitudinally sequential segments, indicated at 38, 40, 42, 44, 46, and 48. As illustrated in FIGS. 2 and 8, each of the conveyor segments 38–48 is comprised of a pair of narrow supporting belts or stainless steel FDA recognized food grade chains 50. Each of the chains 50 has cog serrations on its underside or open links that are engaged by cogs on the toothed driving cog wheels 52 mounted upon drive shafts 56 that are anchored for rotation relative to the sidewalls 14 of the tunnel 12. The chains 50 are looped about the toothed portions of the driving cog wheels 52 and pass about idler gears 54 so that each of the chains 50 forms an endless conveyor loop, as best illustrated in FIG. 3. The driving cog wheels 52 are rotated by the driving shafts 56, which in turn are driven in a conventional manner by a main conveyor system motor through a jack shaft chain with guards (not shown).

The drive shafts 56 are positioned parallel to each other with their axes lying in a horizontal plane. The drive shafts 56 extend the entire width of the irradiation tunnel 12. The portions of the conveyor chains 50 that extend horizontally from one cog wheel 52 to the next define a horizontal linear path of travel 28 for the articles 26 to be treated. The path of travel 28 is preferably about 36 inches above the floor 18 of the irradiation tunnel 12.

As illustrated in FIG. 2, the endless conveyor loops of the chains 50 lie in longitudinally aligned vertical planes 60, 62, 64, 66, 68, and 70 parallel to the article treatment path 28. These planes are spaced apart from each other in a direction perpendicular to the article treatment path 28. Also as illustrated in FIG. 2, the planes in which the endless conveyor loops are aligned on at least two of the different sequential conveyor segments must be offset from each other in a direction perpendicular to the treatment path 28. In the embodiment shown, the endless conveyor loops formed by the chains 50 in each of the conveyor segments 38, 40, 42, 44, 46, and 48 are all offset from each other in a direction perpendicular to the treatment path 28. That is, the chains 50 in each of the conveyor segments 38, 40, 42, 44, 46, and 48 are located at different distances from the walls 14 across the width of the irradiating tunnel 12 so that the underside of an article 26 placed on the conveyor system 24 contacts the chains 50 at different locations across its width as it passes from one conveyor segment to the next.

The areas on the underside of each article 26 that are shielded from radiation emanating from the lower ultraviolet radiation lamps 27 by the belts 50 at the conveyor segment 40 are exposed to radiation by the lower ultraviolet lamps 27 located beneath the next adjacent conveyor segment 42. Actually, in the embodiment shown in the drawing figures any specific areas on the undersides of the articles 26 that are shielded from radiation at any of the conveyor segments 38, 40, 42, 44, 46, and 48 are exposed to radiation from the other lower, ultraviolet lamps beneath all of the other conveyor segments.

To ensure a smooth transition for the articles 26 moving from one conveyor segment to the next, the endless conveyor loops formed by the closed lengths of chain 50 have longitudinally opposing end extremities at the driving cog wheels 52 which propel their advance. As best illustrated in FIGS. 2 and 8, the end extremities of the conveyor loops of each of the conveyor segments 38, 40, 42, 44, 46, and 48 overlap and are interleaved between the end extremities of the conveyor loops of each longitudinally adjacent conveyor segment. That is, the downstream end extremities of the chain loops of the conveyor segment 38 overlap and are interleaved with the chain loops of the upstream end extremities of the conveyor segment 40. The downstream end extremities of the chain loops of the conveyor segment 40 are interleaved with and overlap the upstream ends of the chain loops of the conveyor segment 42, and so forth.

Figure 5:
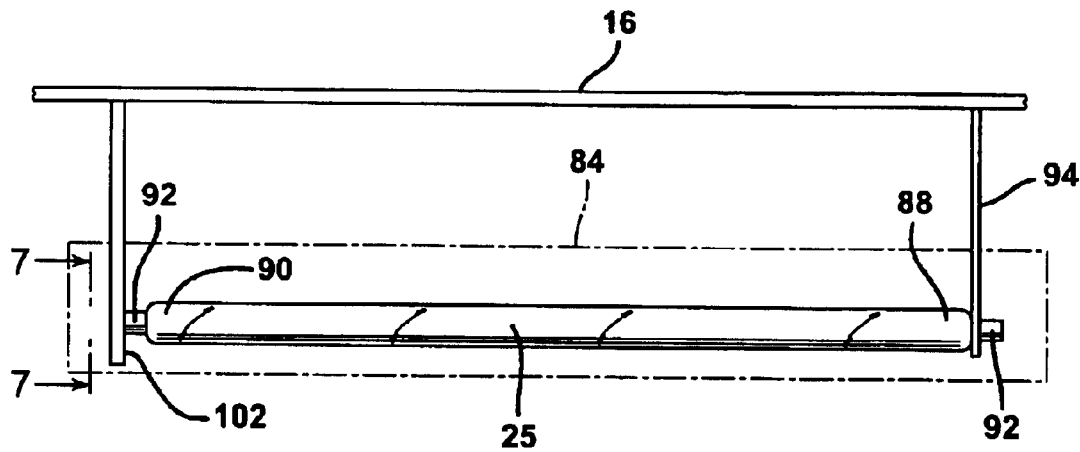
FIG. 5 is a diagrammatic, transverse elevational view of a single ultraviolet irradiation lamp and its mounting supports employed according to the present invention in the irradiation tunnel shown in FIG. 1.

The upper ultraviolet lamps 25 and the lower ultraviolet lamps 27 are mounted perpendicular to the path of travel 28, and extend transversely across the enclosure of the irradiation tunnel 12 between the vertical sides 14 thereof. Each of the lamps 25 and 27 is an elongated, tubular structure and may, for example, be 48 inches in length. The lamps 25 and 27 each have opposing ends that terminate in ceramic sockets 92 as shown in FIG. 5.

Each of the lamps 25 and 27 is provided with a concave, arcuately curved, transversely extending reflector 84 that faces the path of travel 28. The reflectors 84 extend transversely across the width of irradiation tunnel 12, as illustrated in FIG. 1. Since each of the reflectors 84 is concave facing the path of travel 28 of the articles 26 to be treated, the reflectors 84 located beneath the lower ultraviolet lamps 27 are oriented concave upwardly while the reflectors 84 located above the upper ultraviolet lamps 25 face concave downwardly.

Figure 4:
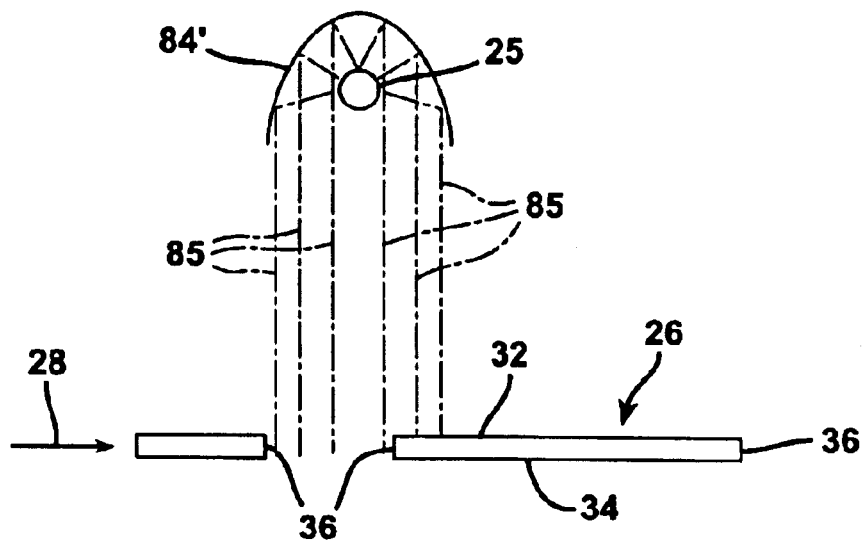
FIG. 4 is a sectional, elevational detail of a single prior art ultraviolet irradiation lamp reflector employed in an ultraviolet irradiation conveyor system.

The reflectors 84 have a different configuration than reflectors currently utilized in ultraviolet irradiation tunnels. FIG. 4 illustrates a conventional, parabolic prior art reflector 84' positioned in association with an upper ultraviolet radiation lamp 25. It should be noted that as the article 26 to be treated advances along its path of travel 28 as shown in FIG. 4, the flat, horizontal surfaces 32 and 34 are exposed to the direct rays of the ultraviolet lamps 25 and 27 and to the parallel, reflected rays 85 that are reflected onto the article 26 by the reflector 84'. However, the vertical surfaces 36 of the article 26, and also any indentations or niches and crevices that may exist within the article 26, are left largely or completely unexposed to radiation.

Figure 4A:
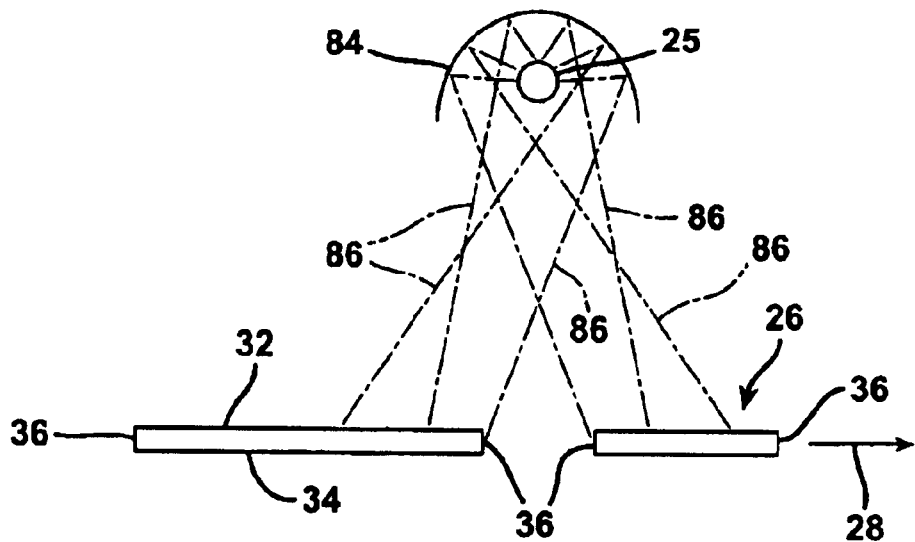
FIG. 4A is a sectional, elevational detail of a single ultraviolet irradiation lamp reflector according to the present invention employed in an ultraviolet irradiation conveyor system.

In contrast, the ultraviolet light irradiation apparatus 10 of the invention does not employ the conventional parabolic reflectors 84', which are illustrated in FIG. 4, but rather employs a plurality of reflectors 84 which are concave and have a nonparabolic cross-sectional arc of curvature. More specifically, in the preferred embodiment as illustrated in FIG. 4A, the reflectors 84 each have an elliptical arc of curvature. The reflectors 84 are located at longitudinally separated locations both above and below the longitudinal path of travel 28 of the article 26.

It can be seen in FIG. 4A that as an article 26 progresses along the path of travel 28 the ultraviolet radiation reflected from each reflector 84 impinges upon the surfaces 32, 34, and 36 of the article 26 at different angles as the article 26 is advanced past the reflector 84 and the ultraviolet lamp located therewithin. The reflected rays 86 in FIG. 4A thereby impinge upon not only the vertical surfaces 36 of the article 26, but also penetrate into any nooks and slots in the article 26, and also upon surfaces that would otherwise be shielded by overhangs and other structures on the article 26.

By utilizing reflectors having a nonparabolic configuration, and reflectors having an elliptical curvature in particular, the ultraviolet light irradiation apparatus 10 directs reflected rays 86 of the ultraviolet light into the intricate webs and cross columns and lateral support members characteristic of many articles 26 to be treated, for example, returnable plastic containers utilized to transport perishable food products. The use of elliptical reflectors 84 also enables reflected ultraviolet light to reach the otherwise "shadowed" areas of indentations, niches, and crannies of more complex structures than the articles 26.

At one point or another along the path of travel 28 virtually all of the surfaces of the article 26 are exposed to direct or reflected ultraviolet radiation from the lamps 25 and 27 and the reflectors 84. As a consequence, the system provides much greater effectiveness in directing ultraviolet radiation onto microorganisms that would otherwise be protected by shadows or lie upon surfaces parallel to the parallel rays 85 reflected by the conventional parabolic reflector 84' shown in FIG. 4.

Figure 6:
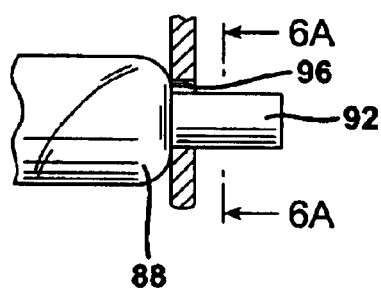
FIG. 6 is a sectional detail of the first end and the support therefor of the ultraviolet irradiation lamp shown in FIG. 5.
Figure 7:
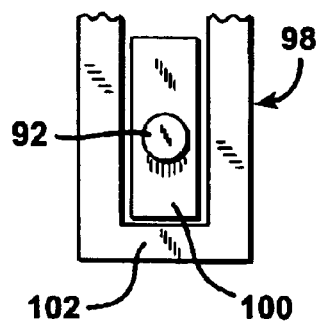
FIG. 7 is an end detail view of the second end of the lamp and support therefor taken along the lines 7—7 in FIG. 5.

FIGS. 5, 6, and 7 illustrate a further unique feature of the ultraviolet light irradiation apparatus 10 of the invention. FIG. 5 illustrates a single one of the transversely oriented, elongated tubular ultraviolet lamps 25 employed in the irradiation tunnel 12. As illustrated in that drawing figure, each of the ultraviolet lamps 25 and 27 has a pair of opposing ends 88 and 90 which are capped with ceramic lamp holders 92. The electrical connections to the lamps 25 and 27 are through these ceramic base holders 92. Each of the ultraviolet lamps 25 and 27 is also provided with a pair of opposing ultraviolet lamp supports for mounting the opposing ends 88 and 90 of each elongated lamp 25 and 27 relative to the tunnel 12.

Figure 6A:
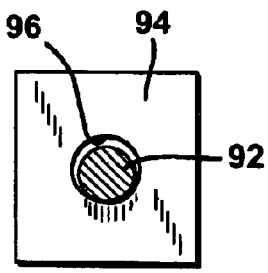
FIG. 6A is a sectional elevational detail view taken along the lines 6A—6A in FIG. 6.

A first of the ultraviolet lamp supports 94 is illustrated in the detailed view of FIG. 6 and is secured relative to the roof 16 of the ultraviolet irradiation tunnel 12. The first lamp end support 94 has a circular opening 96 therethrough to receive the ceramic base 92 at the first end 88 of the lamp 25. As illustrated in FIG. 6A, the circular opening 96 in the first tube support 94 is considerably larger in diameter then the diameter of the cylindrical ceramic base holder 92 located at the first end 88 of the elongated lamp 25. The opening 96 is large enough to permit the elongated tube 25 to be tilted relative to the first support 94.

Each lamp 25 is also provided with a second lamp end support indicated generally at 98. The second lamp end support 98 includes a saddle 102 and a noncircular, oblong block 100 having a rectangular configuration. The block 100 is permanently secured to the outer surface of the ceramic base 92 at the second end 90 of the ultraviolet lamp 25. The saddle 102 defines an upwardly facing channel, as illustrated in FIG. 7, having vertical sides and horizontal bottom.

The U-shaped channel defined in the saddle 102 is configured to receive and snugly seat the rectangular block 100 therewithin. The saddle 102 is secured to the roof 16 of the tunnel 12 at substantially the same height as the first end support 94 so that the opposing ends 88 and 90 of each ultraviolet tube 25 and 27 are secured to the tunnel 12 at the same height. The first supports 94 and the second supports 98 that support the lamps 27 beneath the path of travel project upwardly from the tunnel floor 18.

The ultraviolet tube mounting supports 94 and 98 provide the ultraviolet irradiation apparatus 10 with a unique advantage relative to conventional systems. Specifically, after a period of use, the centers of both the lamps 25 and the lamps 27 will tend to sag, due to the heat generated in producing the ultraviolet radiation for sanitizing the articles 26. This deformation of the otherwise cylindrical structures of the lamps 25 and 27 is detrimental to their performance and reduces the life of the lamps.

To rectify this, it is advisable to rotate each of the lamps 25 and 27 one hundred eighty degrees about its own axis at periodic intervals. This may be easily accomplished, according to the system of the invention, by lifting the rectangular block 100 vertically upwardly out of the channel of the saddle 102 of the second mounting support 98 and rotating the rectangular block 100 about the axis of the tube 25 or 27 through a semicircular arc of one hundred eighty degrees. The opposite end of the rectangular block 100 is then lowered back into the channel of the saddle 102. The oversize circular opening 96 in the first mounting support 94 permits the lamp to be tilted relative thereto and for the first end 88 of the lamp to be rotated freely therewithin. This maintenance procedure can be performed quickly and easily by a single person standing near the second end 90 of each of the lamps 25 and 27. By performing this maintenance procedure on a regular basis, the life of the lamps 25 and 27 can be prolonged considerably.

Undoubtedly, numerous variations and modifications of the invention will become readily apparent to those familiar with sanitizing articles utilizing ultraviolet radiation. For example, reflectors having other nonparabolic shapes may be employed in place of the elliptical reflectors 84. Various nonparabolic shapes will reflect ultraviolet light from the lamp located within its arcuate structure to impinge upon the articles 26 at different angles as the articles 26 progress along their path of treatment 28. Also, the array of the lamps 25 and 27 employed may include ultraviolet lamps of different lengths and different shapes so as to more effectively direct ultraviolet radiation to different locations on the articles 26 being treated. Some of the lamps may be selected to emit a focused beam.

Also, some of the lamps may be oriented at an inclination relative to the path of travel 28, rather than perpendicular thereto. More specifically, preferably at least one of the ultraviolet lamps is arranged with its axis at an angle to the direction of travel of the articles being treated. Indeed, some of the lamps may lie in a vertical plane and may be top angled slightly to depart from parallel alignment to the direction of travel 28 so that the radiation therefrom more effectively reaches complex surfaces on the articles 26. That is, all of the lamps do not necessarily have to reside in a horizontal disposition.

In addition, the speed of the conveyor system 24 is preferably variable so as to allow variations in the ultraviolet radiation dosage given to the articles 26. Accordingly, the scope of the invention should not be construed as limited to the specific embodiment depicted and described, but rather is defined in the claims appended hereto.

I claim:

1. An ultraviolet light irradiation apparatus comprising:
   an irradiation tunnel having an entrance and having an exit longitudinally displaced from said entrance,
   a conveyor system for supporting articles to be irradiated from beneath and for transporting them along a longitudinal treatment path from said entrance to said exit, and including a plurality of different longitudinally sequential segments, whereby said different sequential segments contact different laterally separated locations on said articles from beneath, whereby all locations on said article are left unobscured from beneath at some location on said treatment path within said irradiation tunnel between said entrance and said exit thereof,
   at least one upper ultraviolet irradiation source located within said irradiation tunnel for irradiating said articles from above as they are transported along said treatment path, and
   at least one lower ultraviolet irradiation source for irradiating said articles from beneath at said plurality of different longitudinally sequential segments of said conveyor system.

2. An ultraviolet light irradiation apparatus according to claim 1 wherein each of said different conveyor segments is comprised of a plurality of longitudinally extending, endless conveyor loops lying in parallel, longitudinally aligned vertical planes spaced apart from each other in a direction perpendicular to said treatment path, and the planes in which said endless conveyor loops are aligned on at least two of said different sequential conveyor segments are offset from each other in a direction perpendicular to said treatment path.

3. An ultraviolet light irradiation apparatus according to claim 2 wherein said endless conveyor loops have longitudinally opposing end extremities, and said end extremities of said conveyor loops of each of said conveyor segments overlap and are interleaved between said end extremities of said conveyor loops of each longitudinally adjacent conveyor segment.

4. An ultraviolet light irradiation apparatus according to claim 1 wherein at least some of said ultraviolet irradiation sources are configured as elongated tubes aligned transverse to said longitudinal path of travel, and there are a plurality of said upper ultraviolet radiation tubes located within said tunnel separated longitudinally from each other.

5. An ultraviolet light irradiation apparatus according to claim 4 further comprising elongated tubes of different lengths.

6. An ultraviolet light irradiation apparatus according to claim 1 further comprising ultraviolet irradiation sources having different shapes.

7. An ultraviolet light irradiation apparatus according to claim 1 wherein there is at least one of said lower ultraviolet radiation sources located beneath said treatment path at each of said different longitudinally sequential conveyor segments.

8. An ultraviolet light irradiation apparatus according to claim 1 wherein said conveyor system has a variable speed to vary the amount of ultraviolet radiation to which said articles are exposed.

9. An ultraviolet light irradiation apparatus according to claim 1 wherein at least one of said ultraviolet irradiation sources is configured as an elongated tube aligned transverse to said longitudinal path of travel and said at least one of said ultraviolet radiation tubes is provided with a transversely extending reflector having a concave, nonparabolic cross-sectional arc of curvature and said at least one ultraviolet radiation tube is located within said arc of curvature and between said reflector and said longitudinal path.

10. An ultraviolet light irradiation apparatus according to claim 9 wherein said arc of curvature of said reflector has an elliptical shape.

11. An ultraviolet light irradiation apparatus according to claim 1 wherein at least one of said ultraviolet irradiation sources is an elongated tube having opposing ends and further comprising a pair of opposing ultraviolet tube supports for mounting said opposing ends of said elongated tube relative to said tunnel, wherein a first of said ultraviolet tube supports is secured relative to said ultraviolet irradiation tunnel and has an opening therethrough to receive one of said elongated tube ends, and said second support includes a noncircular constraint secured to the other of said elongated tube ends, and a saddle secured relative to said tunnel at the same height as said first ultraviolet tube support for receiving said noncircular constraint in either of two oppositely oriented dispositions, thereby allowing said elongated tube to be oriented alternatively in either of two oppositely facing directions.

12. An ultraviolet light irradiation apparatus according to claim 11 wherein said noncircular constraint has a rectangular configuration and said saddle defines an upwardly facing channel having vertical sides and a horizontal bottom and is configured to receive and snugly seat said rectangular constraint therewithin.

13. A method of irradiating articles utilizing a conveyor system that transports said articles and supports them from beneath along a longitudinal treatment path from an entrance to an exit of an irradiation tunnel utilizing at least one upper ultraviolet irradiation source located above said longitudinal treatment path and at least one lower ultraviolet irradiation source located beneath said longitudinal treatment path comprising: supporting said articles from beneath and changing the laterally separated points of contact thereon at different longitudinal locations along said tunnel as said articles are transported along said longitudinal treatment path to thereby prevent any parts of said articles facing said irradiation sources from being shadowed from radiation throughout the entire length of said irradiation tunnel.

14. A method according to claim 13 further comprising reflecting at least some of the ultraviolet light from at least one of said ultraviolet irradiation sources to thereby irradiate said articles with reflected ultraviolet light that impinges upon said articles at angles that vary as said articles are transported along said longitudinal treatment path.

15. A method according to claim 13 further comprising subjecting said articles to ultraviolet radiation from beneath using separate irradiation sources located at each of said different longitudinal locations along said tunnel.

\* \* \* \* \*